United States Patent [19]
Akahane et al.

[11] Patent Number: 4,591,384
[45] Date of Patent: May 27, 1986

[54] DENTAL CEMENT COMPOSITIONS

[75] Inventors: Shoji Akahane, Higashikurume; Kazuo Hirota, Tokyo; Kentaro Tomioka, Chofu, all of Japan

[73] Assignee: G-C Dental Industrial Corp., Tokyo, Japan

[21] Appl. No.: 632,462

[22] Filed: Jul. 19, 1984

[30] Foreign Application Priority Data

Aug. 5, 1983 [JP] Japan ................... 58-142515

[51] Int. Cl.$^4$ .............................................. A61K 5/01
[52] U.S. Cl. ..................................... 106/35; 433/228.1
[58] Field of Search ................. 433/199, 228; 106/35; 560/68; 528/1

[56] References Cited

U.S. PATENT DOCUMENTS

| 2,220,950 | 11/1940 | Bird | 252/181 |
| 2,650,194 | 8/1953 | Rahn | 560/68 |
| 2,650,196 | 8/1953 | Rahn | 560/68 |
| 2,653,967 | 9/1953 | Monroe | 560/68 |
| 3,446,733 | 5/1969 | Shell | 252/181 |
| 4,524,824 | 6/1985 | Shimokobe et al. | 106/35 |

Primary Examiner—Lorenzo B. Hayes
Attorney, Agent, or Firm—Oblon, Fisher, Spivak, McClelland & Maier

[57] ABSTRACT

A dental cement composition comprises a first ingredient containing as the main component a metal oxide and a second ingredient capable of reacting with the first ingredient to form a set mass, and further contains a tannic acid derivative that is sparingly soluble in water and a reducing agent that is soluble in water. The instant cement composition may contain an aluminum salt to improve the properties thereof.

9 Claims, No Drawings

DENTAL CEMENT COMPOSITIONS

FIELD OF THE INVENTION

The present invention relates to a dental cement composition, and more especially to an indolent dental cement composition which hardly gives substantial pain to a patient, while it is filled or cemented in his or her mouth, and which hardly suffers substanital discoloration after use and is substantially insoluble in saliva.

BACKGROUND OF THE INVENTION

The present inventors have developed an indolent dental cement containing a tannic acid derivative that is sparingly soluble in water, for which Japanese Patent Application No. 57-64630 was already filed. This dental cement shows a low solubility, and serves to alleviate the pain a great deal during cementation. Although a tannic acid-containing cement discolors, the aforesaid dental cement containing tannic acid derivative being sparingly soluble in water enjoys considerably limited discoloration.

However, it has been found that the aforesaid cement containing tannic acid derivative alone suffers more or less discoloration, inter alia, after the lapse of an extended period of time. The dental cement is designed for such that it starts being set at a point of time at which time it is applied in a patient's oral mouth after mixing. For that reason, it should preferably set in the mouth as soon as possible to give it a large crushing strength and a sufficient time for manipulation until the initial setting takes place. In view of such setting properties, it has also been noted that the aforesaid dental cement containing a tannic acid derivative alone is not necessarily ideal. Furthermore, it has been desired that the dental cement shows a further reduced solubility over an extended period of time in view of its durability.

SUMMARY OF THE INVENTION

A main object of the present invention is therefore to provide a dental cement composition which hardly suffers substantial discoloration over an extended period of time, shows a reduced or limited solubility, and has improved setting properties.

According to the present invention, this object is achieved by the provision of a novel dental cement composition which comprises a tannic acid derivative sparingly soluble in water and further contains a water-soluble reducing agent.

It has been found that the aforesaid composition is further improved by including an aluminium salt.

According to one aspect of the present invention, there is provided a dental cement composition comprising a first ingredient composed mainly of a metal oxide and a second ingredient capable of reacting with the first ingredient to form a set mass, said composition being characterized by containing a tannic acid derivative that is sparingly soluble in water and a reducing agent that is soluble in water.

According to another aspect of the present invention, there is provided the foregoing dental cement composition which is characterized by further containing an aluminium salt.

DETAILED EXPLANATION OF THE INVENTION

In what follows, the present invention will be explained in further detail.

Generally, the dental cement composition comprises a first ingredient composed mainly of a metal oxide and a second ingredient capable of reacting with the first ingredient to form a set mass. In ordinary use, the first ingredient is in the powder or paste form, while the second ingredient is in the liquid, paste or powder form. When the ingredients are both in the powder form they are previously blended together and, in mixing, are adapted to be added with water alone. They are usually mixed together in using except that both ingredients are in a powder form. Alternatively, a part of the second ingredient may be incorporated into the first ingredient. Thus, the dental cement composition may be in the various form with respect to the form of the composition, any limitation is not imposed upon the present invention, and the present invention may be applicable to various combinations of the first ingredient with the second ingredient such as, for instance, powder/liquid, powder/paste, paste/paste, paste/liquid and the like. To add to this, the present invention may also be applicable to a combination of a mixture of the first and second ingredients, both being in the powder form, with water.

The dental cement composition according to the one aspect of the present invention contains a tannic acid derivative that is sparingly soluble in water and a reducing agent that is soluble in water, and the dental cement composition according to the second aspect of the present invention further contains an aluminium salt in addition to the aforesaid two substances. Hereinafter, these three substances may generally be referred to as the additives. The additives may be incorporated into the first and/or the second ingredients. Particularly, it is preferred that the tannic acid derivative and the water-soluble reducing agent are incorporated into the first ingredient.

The metal oxide used as the main component in the first ingredient may include a simple metal oxide such as, for example, zinc oxide or calcium oxide, a combination of a main component zinc oxide with other oxides or fluorides, which is calcined and pulverized, or alternatively a glassy oxide. The term 'glassy oxide' refers to one such as fluoroaluminosilicate glass for dental glass ionomer cements. The metal oxides may be used alone or in combination.

In the present invention, no specific limitation is placed upon the second ingredient capable of reacting with the first ingredient to yield a set mass. As the second ingredient, use may be made of any substance capable of reacting with the first ingredient to yield a set mass. For example, acidic substances such as phosphoric acid or polycarboxylic acid and chelating agents such as cugenol may be employed.

While explanation will be made to the amount of the foregoing additives, it is understood that the amount of the additives given by weight % is based upon the total weight of the composition or based upon the weight of special ingredient after all the additives are incorporated. When the amount of the tannic acid derivative being sparingly soluble in water is in the range of 0.005 to 10 weight % based on the total weight of the dental cement composition, the object of the present invention can be achieved regardless of the form of the first and second ingredients. However, particular preference is given to the range of 0.005 to 5 weight % based on the total weight. When the dental cement composition comprises a combination of the first ingredient in the powder form (which may also be referred to as the cement powder hereinafter) with the second ingredient in the liquid form, satisfactory results are obtained, if the cement powder contains the tannic acid derivative, that is sparingly soluble in water, in an amount of 0.01 to 5 weight % based on the weight of the cement powder. In such a combination, the incorporation of the tannic acid derivative that is sparingly soluble in water is most preferred. The amount of the water-soluble reducing agent is 0.005 to 5 weight %, preferably 0.005 to 3 weight % based on the total weight of the composition. It is particularly preferred that the cement powder contains the water-soluble reducing agent in an amount which is within the aforesaid range and ranges from 0.01 to 5 weight % based on the weight of the first ingredient. The amount of the aluminium salt is 0.005 to 5 weight %, preferably 0.005 to 3 weight % based on the total weight of the composition.

The wording 'tannic acid derivative being sparingly soluble in water' refers to one that is hardly or slightly soluble in water, and particularly includes a tannic acid/protein combination, a tannic acid/formaldehyde combination, acetyl tannate and a metal tannate, which may be used alone or in combination. Proteins are generally the polycondensates of amino acids. The proteins which can be used in the present invention may be of either simple or conjugated type. For example, use may be made of simple proteins such as protamin, globulin, albumin, glutelin, prolamin, gelatin and the like as well as conjugated proteins such as nucleoprotein, phosphoprotein and the like. Of these proteins, particular preference is given to albumin and gelatin. It is noted that no specific limitation is placed upon the tannic acid salts of metals. However, use may be made of, e.g., calcium, aluminium, zinc, magnesium, strontium and the like salts. As the metal salts, are preferred, aluminium, zinc and calcium salts.

The water-soluble reducing agent used in the present invention may include, for instance, salts of tin in a low valency state, aldehydes, saccharides, reducing organic compounds such as formic acid or oxalic acid, and salts of a lower oxyacid such as phosphorous acid or hypophosphorous acid. Particular preference is given to stannous sulfate, chloride or fluoride. The water-soluble reducing agents may be used alone or in combination.

The aluminium salt used in the present invention may include, for instance, aluminium sulfate, nitrate, chloride, fluoride and citrate as well as alum. These aluminium salts may be used alone or in combination.

The dental cement formulation according to the present invention has the aforesaid composition, so that it is not only indolent but also of more rapid in setting. In addition, the present formulation has a large crushing strength, shows an initial setting period sufficient for manipulation, and hardly suffers substantial discoloration or dissolution over an extended period of time after use.

When preparing the dental cement formulation according to the present invention, for example, zinc phosphate cement, silicate cement, cugenol cement, glass ionomer cement, polycarboxylate cement and the like may be added to the aforesaid composition.

The present invention will now be explained in further detail with reference to the examples, which are given for the purpose of illustration alone.

EXAMPLE 1

Albumin tannate 0.5 grams, stannous chloride 0.5 grams, potassium alum 0.5 grams and a carboxylate cement powder ("Carbolit 100" Powder manufactured and sold by G-C Denta Industrial Corp.) 98.5 grams were uniformly blended together in a ceramic mortar to form a cement powder. This cement powder was mixed with a polycarboxylate cement setting liquid ("Carbolit 100" Liquid manufactured and sold by G-C Dental Industrial Corp.) in a proportion of 1.7 to 1.0 to form a dental cement composition. This cement composition was mixed together, and immersed in pure water to measure the solubility and crushing strength thereof after the lapse of one day according to testing method of JIS T6602. The discoloration of the set mass was also observed after the lapse of one month from mixing.

EXAMPLES 2-4

To prepare three dental cement compositions, the procedures of Example 1 were repeated, provided that the amounts of stannous chloride and potassium alum were kept constant at 0.5 grams respectively, while the amount of albumin tannate was 0.1 grams, 1.0 gram and 2.0 grams with the amount of the carboxylate cement powder being 98.9 grams, 98.0 grams and 97.0 grams correspondingly. The solubility and crushing strength of each composition after one-day setting as well as the discoloration of each composition after one month were measured according to the test procedures described in Example 1.

EXAMPLES 5 and 6

To prepare two dental cement compositions, the procedures of Example 1 were repeated, provided that the amounts of albumin tannate and potassium alum were kept constant at 0.5 grams respectively, while the amount of stannous chloride was 0.1 grams and 1.0 garm with the amount of the carboxylate cement powder being 98.9 grams and 98.0 grams, correspondingly. The solubility and crushing strength of each composition after one-day setting as well as the discoloration of each composition after one month were also measured in a manner similar to that described in Example 1.

EXAMPLE 7

To prepare a dental cement composition, the procedures of Example 1 were repeated, provided that aluminim tannate 0.5 grams, stannous chloride 0.5 grams and a polycarboxylate cement powder 99.0 grams were used without using potassium alum. The solubility and crushing strength of the composition after one-day setting as well as the discoloration thereof after one month were measured.

COMPARATIVE EXAMPLES 1 AND 2

The procedures of Example 2 were repeated, provided that stannous chloride and potassium alum were not used (Comparative Example 1), and albumin tannate, stannous chloride and potassium alum were not used (Comparative Example 2). In a manner similar to that described in Example 2, the solubility, crushing strength and discoloration of each set mass were examined.

The results are shown in Table 1.

TABLE 1

| No. of Example | Amount of Tannic Acid Derivative * in Gram | Amount of Stannous Chloride in Gram | Amount of Potassium Alum in Gram | Solubility after 1 day in Percent | Crushing Strength after 1 day in kg/cm$^2$ | Discoloration after 1 month |
| --- | --- | --- | --- | --- | --- | --- |
| 1 | 0.5 | 0.5 | 0.5 | 0.01 | 940 | None |
| 2 | 0.1 | 0.5 | 0.5 | 0.03 | 880 | None |
| 3 | 1.0 | 0.5 | 0.5 | 0.01 | 960 | None |
| 4 | 2.0 | 0.5 | 0.5 | 0.01 | 980 | None |
| 5 | 0.5 | 0.1 | 0.5 | 0.02 | 930 | Very Slight |
| 6 | 0.5 | 1.0 | 0.5 | 0.01 | 950 | None |
| 7 | 0.5 | 0.5 | 0.5 | 0.01 | 910 | None |
| Comparative Ex. 1 | 0.1 | 0 | 0 | 0.04 | 850 | Slight |
| Comparative Ex. 2 | 0 | 0 | 0 | 0.05 | 840 | None |

* Ex. 1–6: Albumin tannat;
Ex. 7: Aluminium tannate

From Table 1, it is found that all the compositions according to the present invention are markedly improved in respect of the degree of discoloration after one month compared with the composition of Comparative Example 1, which contained albumin tannate alone, and are superior to the compositions of Comparative Examples 1 and 2 in solubility and crushing strength.

EXAMPLES 8 AND 9

In Examples 1 and 3, stannous fluoride in place of stannous chloride was blended to polycarboxylate cement powder (Carbolit 100 powder). Composition is 0.5 gram albumin tannate, 0.5 gram stannous fluoride, 99.0 gram Carbolit 100 powder in Example 8 and 1.0 gram albumin tannate, 0.5 gram stannous fluoride, 98.5 gram Carbolit 100 powder in Example 9. Potassium alum was not blended in these examples. But 0.5 gram aluminium chloride (AlCl$_3$6H$_2$O) was dissolved to a polycarboxylate cement liquid (Carbolit 100 liquid manufactured and sold by G-C Dental Industrial Corp.). These powder and liquid were mixed in a powder to liquid ratio of 1.7 gams to 1.0 gram. The solubility, crushing strength and discoloration were measured according to the test method in Example 1. Solubility was 0.01 % in both examples. Crushing strength is 950 kg/cm$^2$ and 980 kg/cm$^2$ in Examples 8 and 9 respectively. There was no discoloration in both examples. The results of both examples are superior to these of Comparative Examples 1 and 2.

TABLE 2

| No. of Example | Amount of albumin tannate (g) | Amount of stannous Fluoride (g) | Amount of aluminum chloride* (g) | Solubility after 1 day (%) | Crushing strength after 1 day (kg/cm$^2$) | Discoloration after 1 month |
| --- | --- | --- | --- | --- | --- | --- |
| 8 | 0.5 | 0.5 | 0.5 | 0.01 | 950 | None |
| 9 | 1.0 | 0.5 | 0.5 | 0.01 | 980 | None |

*Dissolved in the liquid.

EXAMPLE 10

Aluminium tannate 0.5 grams and stannous chloride 0.5 grams were mixed with a dental glass ionomer cement powder ("Fuji Ionomer Type I" Powder manufactured and sold by G-C Dental Industrial Corp.) 99.0 grams to form a cement powder. Using as the setting liquid a dental glass ionomer cement setting liquid ("Fuji Ionomer Type I" Liquid manufactured and sold by G-C Dental Industrial Corp.), a dental cement composition was prepared, provided that a powder/liquid ratio was 1.4 to 1.0. This composition was mixed to form a set mass whose initial setting time, solubility and crushing strength after one-day setting were measured. After the lapse of one month, the discoloration of the set mass was also measured.

EXAMPLE 11

To prepare a dental cement composition, the procedures of Example 10 were repeated, provided, in the preparation of a cement powder, calcium tannate 0.5 grams were used in place of aluminium tannate 0.5 grams, and aluminium sulfate 0.4 grams were further added with the amount of the glass ionomer cement powder being adjusted to 98.6 grams, correspondingly. The obtained composition was mixed and set to measure the physical properties thereof.

EXAMPLE 12

To prepare a dental cement composition, the procedures of Example 10 were repeated, provided that, in the preparation of a cement powder, aluminium tannate 0.3 grams and albumin tannate 0.5 grams were simultaneously used in place of aluminium tannate 0.5 grams, and aluminium sulfate 0.4 grams were further added with the amount of the glass ionomer cement powder being adjusted to 98.3 grams, correspondingly. The obtained composition was mixed and set to measure the physical properties thereof.

COMPARATIVE EXAMPLE 3

In Example 10, only the dental glass ionomer cement powder was used as the cement powder to form a composition which was then mixed and set to measure the physical properties thereof.

COMPARATIVE EXAMPLE 4

The procedures of Example 10 were repeated, provided that a mixture of the dental glass ionomer cement powder 99.8 grams with aluminium tannate 0.2 grams. The obtained composition was measured on its physical properties in a manner similar to that described in Example 10.

The results of Examples 10-12 and Comparative Examples 3-4 are shown in Table 3.

TABLE 3

|  | Initial Setting Time (Min.) | Crushing Strength ($Kg/Cm^2$) | Solubility (%) | Discoloration after 1 month |
|---|---|---|---|---|
| Example 10 | 5.5 | 1460 | 0.2 | None |
| Example 11 | 5.0 | 1480 | 0.1 | None |
| Example 12 | 5.0 | 1490 | 0.1 | None |
| Compara. Example 3 | 5.5 | 1420 | 0.6 | None |
| Compara. Example 4 | 5.5 | 1440 | 0.4 | Slight |

As will be noted from Table 3, the compositions of Examples 10-12 are all lower in solubility and slightly higher in crushing strength than those of Comparative Examples 3-4. The instant compositions show an initial setting time substantially equal to those of Comparative Examples 3-4, which time is sufficient for manipulation, and suffer no discoloration after use.

What is claimed is:

1. In a dental cement composition comprising:
   (a) a first ingredient containing as the main component a metal oxide and
   (b) a second ingredient capable of reacting with the first ingredient to form a set mass, the improvement comprising, as said second ingredient, a mixture of;
   (I) a tannic acid derivtive that is sparingly soluble in water selected from the group consisting of a tannic acid/protein complex, a tannic acid/formaldehyde reaction product, acetyl tannate, a metal tannate or a mixture thereof, and
   (II) a water-soluble reducing agent selected from the group consisting of a stannous tin salt, formic acid, oxalic acid and a salt of phosphorous or hypophosphorous acids.

2. The composition of claim 1, wherein the amounts of said tannic acid derivative and said reducing agent are in the ranges of 0.005 to 10 weight % and 0.005 to 5 weight %, respectively, based on the total weight of said composition.

3. The composition of claim 2, wherein said tannic acid derivative and said reducing agent are incorporated into the first ingredient.

4. The composition of claim 3, wherein the amounts of said tannic acid derivative and said reducing agent are in the ranges of 0.01 to 5 weight % and 0.01 to 5 weight %, respectively, based on the weight of the first ingredient.

5. In a dental cement composition comprising
   (a) a first ingredient containing a metal oxide as the main component and
   (b) a second ingredient capable of reacting with the first ingredient to form a set mass, the improvement comprising, as said second ingredient, a mixture of;
   (I) a tannic acid derivative that is sparingly soluble in water selected from the group consisting of a tannic acid/protein complex, a tannic acid/formaldehyde reaction product acetyl tannate, a metal tannate or a mixture thereof,
   (II) a water-soluble reducing agent selected from the group consisting of a stannous tin salt, formic acid, oxalic acid and a salt of phosphorous or hypophosphorous acids, and
   (III) an aluminium salt.

6. The composition of claim 5, in which the amounts of said tannic acid derivative, said reducing agent and said aluminium salt are 0.005-10% by weight, 0.005-5% by weight and 0.005-5% by weight, respectively, based on the total weight of said composition.

7. The composition of claim 6, in which said tannic acid derivative and said reducing agent are both contained in the first ingredient.

8. The composition of claim 7, in which the amounts of said tannic acid derivative and said reducing agent are in the ranges of 0.01-5% by weight and 0.01-5% by weight, respectively, based on the weight of the first ingredient.

9. A composition as defined in claim 5, in which said aluminium salt is one or more selected from the group consisting of aluminium sulfate, aluminium nitrate, aluminium chloride, alum, aluminium citrate and aluminium fluoride.

* * * * *